(12) United States Patent
DeVincenzo et al.

(10) Patent No.: US 7,559,764 B2
(45) Date of Patent: *Jul. 14, 2009

(54) ORTHODONTIC BONE ANCHOR

(75) Inventors: John DeVincenzo, 1312 Garden St., San Luis Obispo, CA (US) 93401; Craig Jacobson, Encinitas, CA (US); Steven O. Luse, Vista, CA (US)

(73) Assignee: John DeVincenzo, San Luis Obispo, CA (US)

( * ) Notice: Subject to any disclaimer, the term of this patent is extended or adjusted under 35 U.S.C. 154(b) by 464 days.

This patent is subject to a terminal disclaimer.

(21) Appl. No.: 11/021,808

(22) Filed: Dec. 27, 2004

(65) Prior Publication Data
US 2005/0147938 A1    Jul. 7, 2005

Related U.S. Application Data

(60) Provisional application No. 60/534,467, filed on Jan. 6, 2004.

(51) Int. Cl.
*A61C 3/00* (2006.01)
*A61C 8/00* (2006.01)

(52) U.S. Cl. .................................. 433/18; 433/173
(58) Field of Classification Search ................ 433/18, 433/172–176
See application file for complete search history.

(56) References Cited

U.S. PATENT DOCUMENTS

| 5,853,291 | A | * | 12/1998 | DeVincenzo et al. | ........ 433/176 |
| 5,921,774 | A | * | 7/1999 | Kanomi et al. | ................ 433/18 |
| 6,193,509 | B1 | * | 2/2001 | DeVincenzo | ................ 433/18 |
| 6,354,834 | B2 | * | 3/2002 | Kanomi et al. | ................ 433/18 |
| 7,281,923 | B1 | * | 10/2007 | DeVincenzo et al. | .......... 433/18 |
| 2003/0104335 | A1 | * | 6/2003 | Chung | ......................... 433/18 |
| 2004/0147931 | A1 | * | 7/2004 | De Clerck | .................... 606/70 |

* cited by examiner

*Primary Examiner*—John J Wilson
(74) *Attorney, Agent, or Firm*—Rodgers & Rodgers

(57) ABSTRACT

An orthodontic bone anchor includes a bone plate, a narrow extension extending from one end of the bone plate, a cap enveloping the extension, and a pair of arms extending outwardly from the cap.

16 Claims, 6 Drawing Sheets

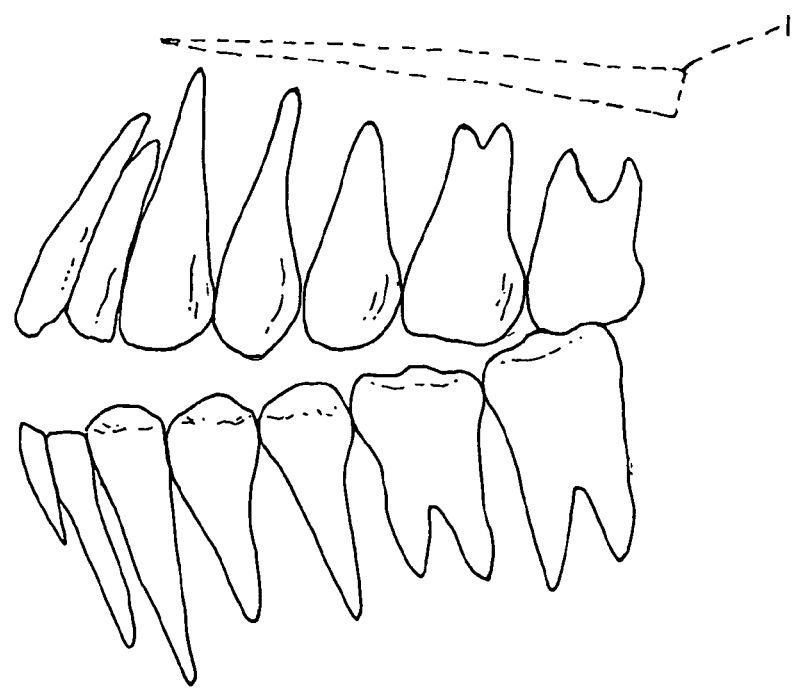
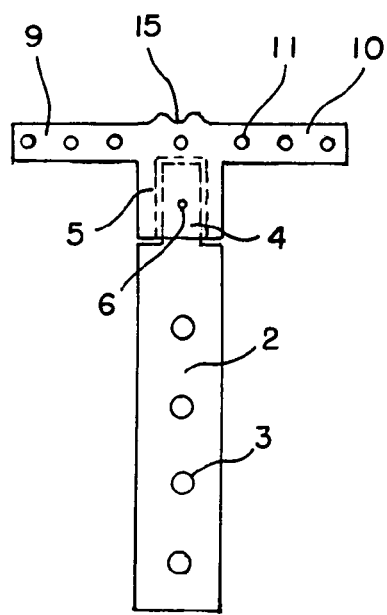
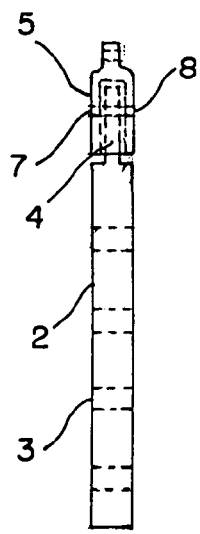
FIG. 1
FIG. 2
FIG. 3

ORTHODONTIC BONE ANCHOR

The benefits under 35 U.S.C. 119 are claimed of U.S. provisional patent application 60/534,467 filed Jan. 6, 2004.

BACKGROUND OF THE INVENTION

In orthodontics, one type of malocclusion is encountered in which an anterior openbite is caused by occlusal contacts only occurring posteriorly. The standard method to correct this kind of malocclusion is with surgical intervention whereby a wedge of bone is removed from the maxilla apical to the maxillary root tips. After removal of the wedge of bone, autorotation of the mandible will occur thereby correcting the anterior openbite. It is the intent of this invention to eliminate this surgical procedure and provide a device which selectively intrudes the posterior teeth of both the maxilla and mandible and thereby facilitates the closure of anterior openbite malocclusions by autorotation.

Umemori et al, (Am J Orthod Dentofacial Orthop, 115: 166, 1999), in 1999, first described a bone anchor system to intrude posterior teeth and facilitate correction of an anterior openbite without surgery. Several years later, Sherwood, in 2002, (Sherwood, K H et al., Am J Orthod Dentofacial Orthop, 122:593, 2002) and 2003, (Sherwood, KH et al., (Angle Orthod, 73:597, 2003), described similar mechanisms to facilitate anterior rotation and closure of an anterior openbite. Additional descriptions of similar approaches were described by Erverdi, (Erverdi, N et al., World J. Orthod, 3:147, 2002) in 2002 and by Miyawaki, S et al., (Am J Orthod Dentofacial Orthop, 124:84, 2002) in 2003. An overall review of orthodontic anchorage in general, including specific references to bone plates, was completed by Favero, (Favero, L et al., Am J Orthod Dentofacial Orthop 122:84, 2002) in 2002.

In all of these systems, the bone plate has an extension into the vestibule from which materials or springs are attached to facilitate intrusion of the posterior teeth. The disadvantage to all of the previous methods is that the point of force application cannot be changed during treatment nor can the bone anchor be modified or adjusted prior to insertion or during treatment. A change in the location of force application to the dentition is often required and without a corresponding change on the anchor a different and generally undesirable change in the vector of this force occurs. This change in vector can limit the extent of correction of anterior openbites. If the centroid of the maxillary arch varies from the point of force application, a moment occurs and the resultant rotation around the centroid could actually open the bite thus making the malocclusion worse.

In practice, the surgeon often encounters difficulty in placing the bone plate as distally as desired. Additionally, the clinician attaching the elastomeric materials or springs from the bone plate to the dentition experiences difficulty when the bone plates are placed too far posteriorly. Often, the surgeon has difficulty placing the anchors in the correct location to achieve the desired point of emergence of the bone plate into the vestibule. This variation in height and location of the bone plate for subsequent tooth movement presents significant difficulties to the clinician attempting to intrude the posterior teeth.

An adjustable and/or removable cap on the bone plate permits the surgeon to place the bone plate in a more accessible region of the mouth while extensions from the cap can be used to move the point of force application to the dentition in the most desirable location, i.e., the centroid. By utilizing different configurations for the cap, the point of emergence of the bone plate from the vestibule becomes less critical thus facilitating a more clinically acceptable method of intruding the posterior teeth.

SUMMARY OF THE INVENTION

An adjustable bone anchor has a fixed plate attached to bone at a distance from its emergence into the buccal vestibule of a patient. The bone plate is attached by screws or other osseointegrated anchors to the bone. Attached to the protruding portion of the plate is an extension or cap, which can be removed, adjusted or replaced as desired. The supragingival cap has a series of small holes or indentations through which or under which elastomeric material or coil springs can pass or attach for the purpose of applying force to the surrounding dentition. The supragingival cap varies in size and shape and is adjustable before final attachment to the bone plate by a variety of means such as ligature wire, a pin, a spring clip, a tapped screw, etc. Removal of the supragingival cap during orthodontic movement is easily facilitated and adjustments made thereto or the cap replaced with a supragingival cap having a different configuration.

BRIEF DESCRIPTION OF THE SEVERAL VIEWS OF THE DRAWINGS

In the drawings:

FIG. 1 is a side view showing an anterior openbite;

FIGS. 2 and 3 are elevational views showing one form of the bone anchor according to this invention;

FIG. 6 is an elevational view of a modification of the invention;

DETAILED DESCRIPTION OF THE INVENTION

Figure 4:
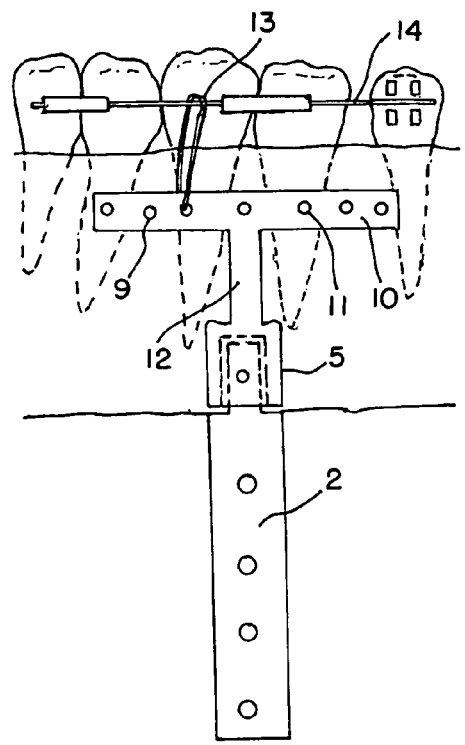
FIGS. 4, 5 and 6 depict an orthodontic application of the invention as applied to the mandible.

With reference to FIG. 1, an anterior openbite is shown. Historically, an openbite, which is caused by posterior occlusal contacts, was corrected by removal of bone wedge 1 from the maxilla apical to the maxillary root tips. Following surgery, autorotation results in correction of the openbite.

In FIGS. 2 and 3, titanium bone plate 2 is shown which is attached by means of bone screws inserted through apertures 3 into the bone. Protruding end 4 of bone plate 2 is narrowed and supragingival cap 5 is fitted over it. A small aperture 6 is formed in bone plate 2 and a small diameter ligature wire or pin or screw, if the aperture is tapped, is inserted through apertures 7 and 8 in cap 5 and aperture 6 in protruding end 4 of bone plate 2 to secure cap 5 to bone plate 2. Arms 9 and 10 extend outwardly from cap 5 and include apertures 11.

Supragingival cap 5 comes in a variety of lengths and heights and the appropriate one can be selected to meet the requirements of a particular patient before attachment to bone plate 2 by means of ligature wire, a pin, spring clip or screw if the aperture is tapped. As best viewed in FIG. 3, bone plate 2, extension 4 and cap 5 are flat and planar in configuration and disposed in the same plane when fully assembled.

Figures 5, 6:
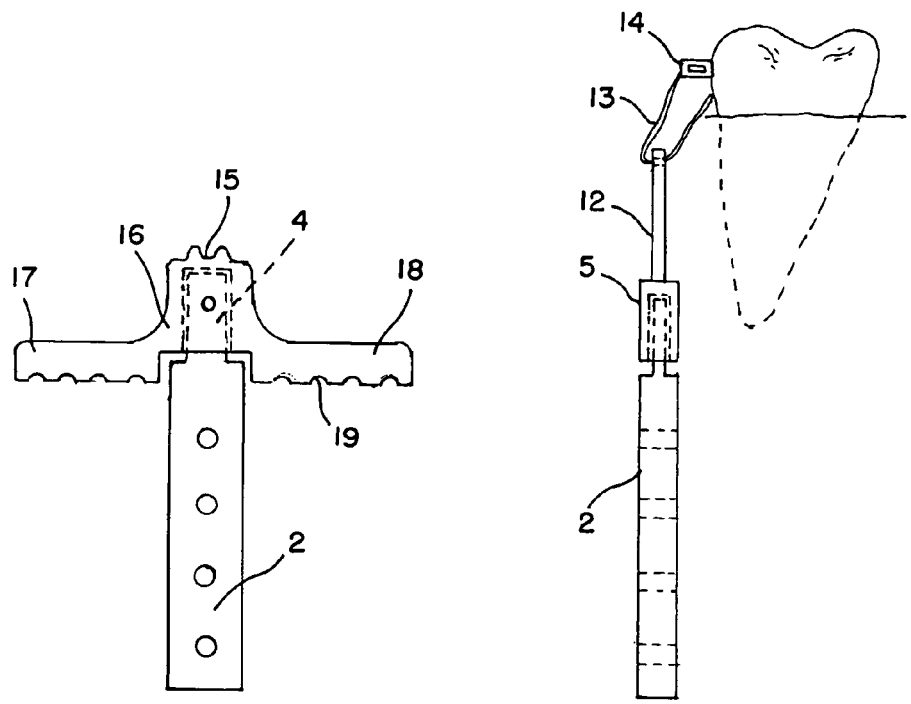

A modified version of cap 5 includes neck 12 extending upwardly from bone plate 2 as illustrated in FIGS. 4 and 5 wherein elastomeric or spring material 13 is threaded through one or more of the apertures 11 formed in arms 9 and 10 and then attached to archwire 14. By this means, intrusion of the posterior teeth is facilitated in a variety of locations and directions based on the observations of the clinician. Also, small groove 15 helps maintain the ligature wire, which secures cap 5 to bone plate 2, in place.

In FIG. 6, a modification of the invention is shown wherein cap 16 envelops end 4 of bone plate 2 and includes laterally extending arms 17 and 18. Multiple indentations 19 are formed along the lower edges of arms 17 and 18 for the purpose of receiving elastomeric or other like spring means 13.

Figure 7:
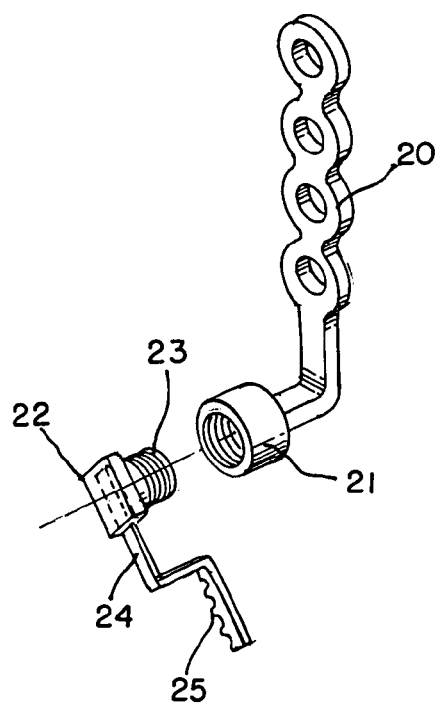
FIGS. 7-15 are perspective views of further modifications of the bone anchor attached to the maxilla.

Another modification is shown in FIG. 7 with attachment of the bone plate 40 to the maxilla, wherein bone plate 20 is provided which extends downwardly with the lower end thereof disposed at a right angle thereto with interiorly threaded cap 21 affixed to the end thereof. Angular attachment tube 22 is secured to screw 23 which is screwed into threaded cap 21. One end of attachment bar 24 is inserted into attachment tube 22 with the opposite end offset therefrom and extending parallel hereto and which includes indentations 25. Of course, attachment bar 24 may be bent in a variety of directions. Then appropriate spring means is looped over attachment bar 24 and maintained in position by means of indentations 25.

Figure 8:
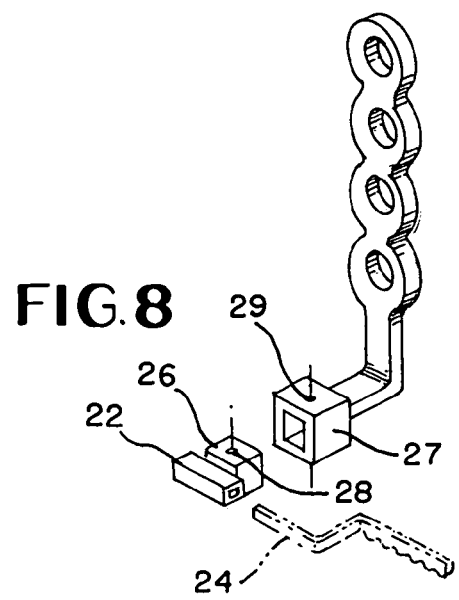

A similar configuration to that shown in FIG. 7 is shown in FIG. 8 wherein angular attachment tube 22 is secured to attachment square 26. Attachment square 26 is inserted into square cap 27 which is attached to bone plate 20 and wherein the two are secured together by means of a wire inserted through aperture 28 on the top of attachment square 26 and aperture 29 formed in the top of the square cap 27 and the corresponding apertures formed in the bottoms thereof.

Figure 9:
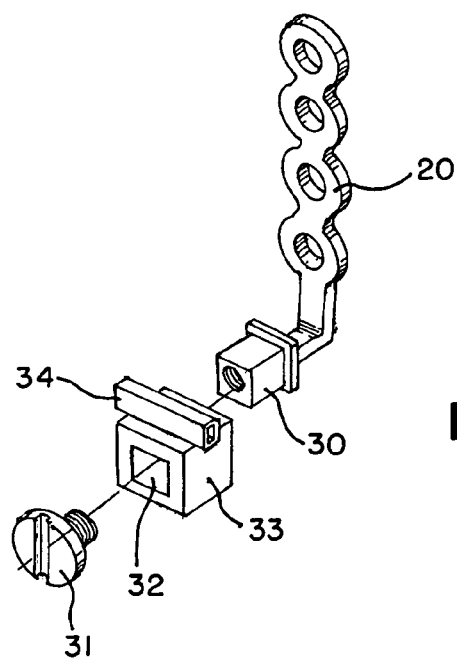

In FIG. 9, square cap 30 is attached to the lower right angle portion of bone plate 20 and is threaded interiorly and is adapted to receive screw 31. Aperture 32 is formed in attachment block 33. To complete the assembly, attachment block 33 is simply slipped over square cap 30 and then screw 31 is threaded into square cap 30 to secure the two together. Angular attachment tube 34 is secured to attachment block 33 for the purpose as discussed above in connection with FIG. 7.

Figure 10:
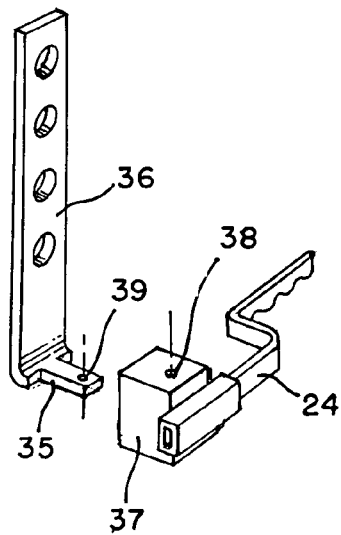

By the modification shown in FIG. 10, attachment tab 35 extends perpendicularly from the lower edge of bone plate 36 and is adapted to receive attachment cap 37. Then a wire, pin or spring clip is inserted through apertures 38 and 39 and the corresponding aperture in the bottom portion of cap 37 to secure attachment cap 37 onto attachment tab 35.

Figure 11:
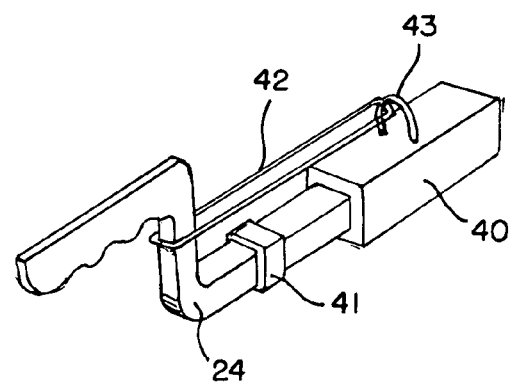

In order to attach attachment bar 24 securely to an angular tube such as shown in FIGS. 7-10, attachment bar 24 is inserted into angular tube 40 as shown in FIG. 11. Adjustable ring 41 is provided so as to prevent attachment bar 24 from sliding too far into angular tube 40. Then a small wire or other material 42 is secured on attachment bar 24 to the angular tube 40 by using loop 43.

Figure 12:
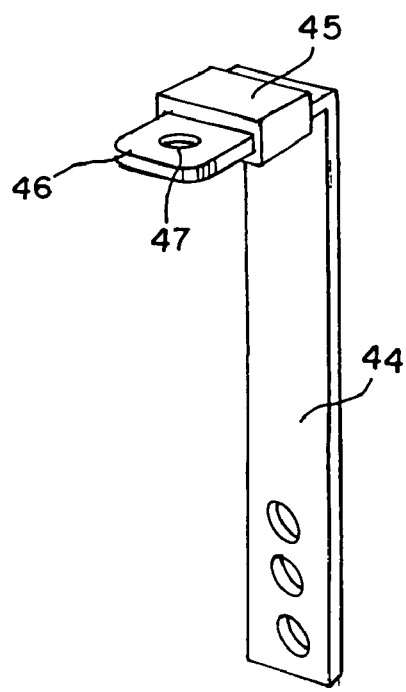

In FIG. 12, bone anchor 44 is shown wherein sliding cap 45 is fitted around right angle protrusion 46. Aperture 47 is formed in protrusion 46 in order to receive a brass pin, ligature wire, spring clip or light cured material which is placed and cured. All of these means serve to secure sliding cap 45 in place.

Figure 15:
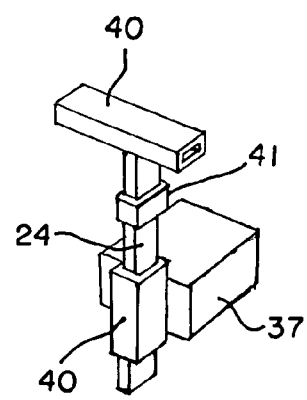
Figure 13:
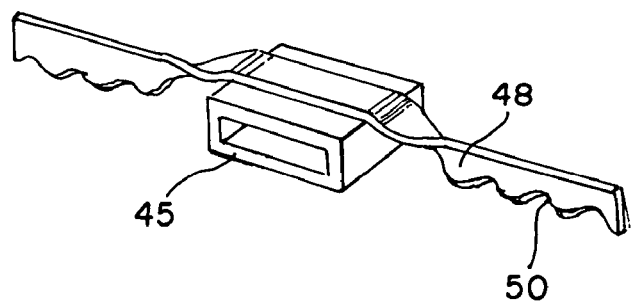
Figure 14:
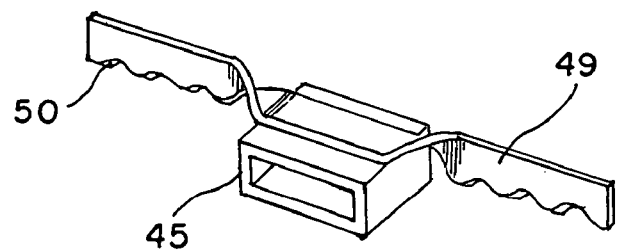

In FIGS. 13 and 14, shaped attachments 48 and 49 are secured to sliding cap 45. Of course, elastomeric or spring material is positioned in the indentations 50, as desired. A further modification of the invention is shown in FIG. 15 wherein a further modification includes attachment bar 24 which is generally vertically disposed and secured to angular tube 40.

Figure 16:
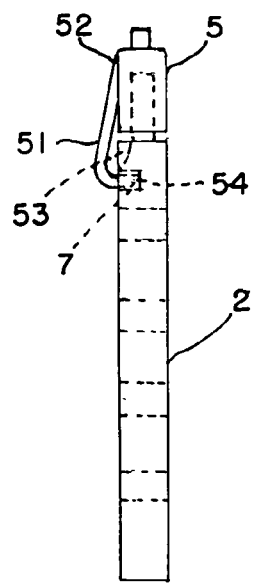
FIGS. 16-19 show additional modifications of the bone anchor.

A further modification of the invention is shown in FIG. 16 wherein L-shaped spring clip 51 is attached to cap 5 by means of laser weld 52 with the end opposite from weld 52 being inserted into aperture 7 and, when completely seated, being securely locked in place. Spring clip 51 is manufactured of a highly flexible material such as a titanium alloy. To remove cap 5 from the bone plate 2, a sharp rectangular instrument is inserted under spring clip 51 and rotated in such a manner that spring clip 51 is moved out of aperture 7 (as viewed in FIG. 16) thereby permitting removal of cap 5 from bone plate 2. To insert cap 5 onto bone plate 2, a curved groove in the apical end 53 of bone plate 2 forces spring clip 51 to open as internal edge 54 slides in the groove formed in end 53 when cap 5 is pressed basally.

Figure 17:
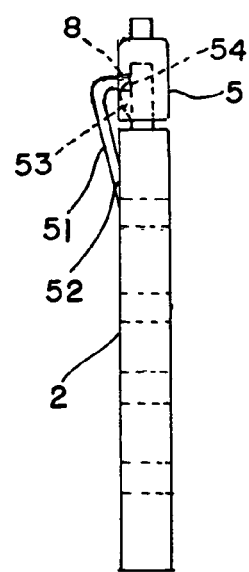

Conversely, spring clip 51, shown in FIG. 17, can be welded to bone anchor 2 and inserted into cap 5 by way of aperture 8. On insertion of cap 5 onto bone plate 2, groove 53 helps deflect clip 51, by means of bevel 54, to aid in the insertion process. Removal of cap is as described in connection with FIG. 16.

Figure 18:
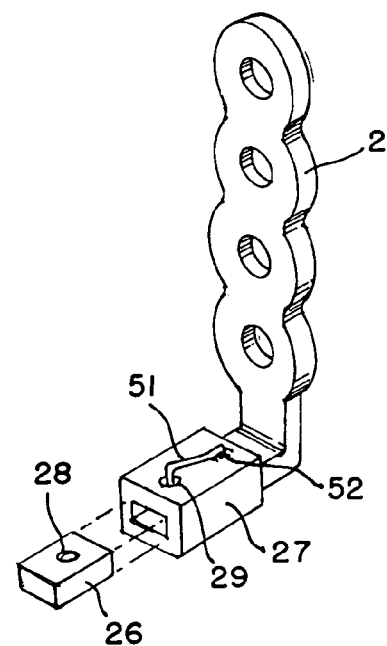

In FIG. 18, spring clip 51 is attached to angular apical end 27 of bone plate 2 by means of weld 52. Attachment angular block 26 includes a beveled surface to urge spring clip 51 upwardly from aperture 29 as attachment angular block 26 moves into angular apical end 27 when aperture 28 becomes aligned with aperture 29, spring clip 51 then snaps into aperture 28 thereby securing angular block 26 to angular apical end 27.

The same structure as shown in FIG. 18 could be utilized in connection with the means shown in FIG. 10 wherein the spring clip is attached to attachment cap 37 at the buccal surface with aperture 38 as close to the lingual surface of cap 37 as possible. Attachment tab 35 and the end of the spring clip are beveled to facilitate manipulation of the spring clip.

Figure 19:
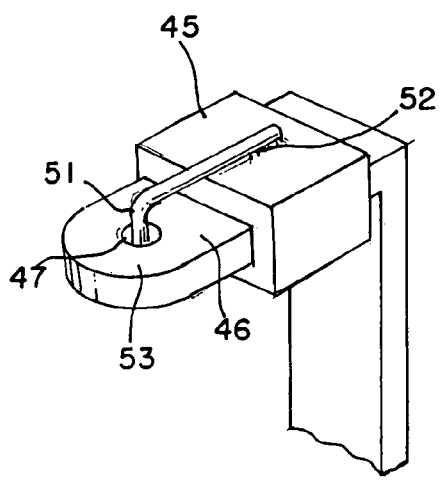

Finally, in FIG. 19, protrusion 46 corresponds generally to that shown in FIG. 12 wherein spring clip 51 is attached to cap 45 by means of weld 52 and projects through aperture 47. Spring clip 51 is removed from aperture 47 by insertion of a rectangular instrument under spring clip 51.

As orthodontic treatment progresses, resistance to intrusion varies along the dentition depending on a number of factors including surface area to resistance, varying metabolic activity surrounding particular roots, root position relative to cortical verses alveolar bone, etc. By having an adjustable cap, which is also replaceable by other types of caps, if desired, the clinician is able to maintain the optimal force vector for optimum intrusion along the entire posterior occlusal plane.

We claim:

1. An orthodontic bone anchor comprising a planar bone plate, apertures formed in said bone plate for attachment to bone, a supragingival planar extension formed on one end of said bone plate, said extension being narrower in width than the width of said bone plate, a removable planar cap enveloping said extension, the width of said bone plate being substantially the same as the width of said cap, at least one planar arm extending outwardly from said cap, said bone plate and said extension and said arm being disposed in the same plane, and at least one indentation formed on one edge of said arm.

2. An orthodontic bone anchor according to claim 1 wherein said cap is attached to said bone plate by means of ligature wire.

3. An orthodontic bone anchor according to claim 2 wherein apertures are formed in said cap and bone plate and said ligature wire is insertable therethrough.

4. An orthodontic bone anchor according to claim 1 wherein at least one aperture is formed in said arm.

5. An orthodontic bone anchor according to claim 1 wherein a pair of arms extend outwardly from said cap.

6. An orthodontic bone anchor according to claim 5 wherein a groove is formed in said cap midway between said arms.

7. An orthodontic bone anchor according to claim 1 wherein said cap is angular in shape and wherein attachment means is adapted to envelop said cap and wherein said attachment means is secured to said cap by means of a screw.

8. An orthodontic bone anchor according to claim 1 wherein said cap is attached to said bone plate by means of a pin, apertures are formed in said cap and bone plate, and said pin is insertable therethrough.

9. An orthodontic bone anchor according to claim 1 wherein a pair of apertures are formed respectively in said extension and said cap and a spring clip is attached to said cap at one end and insertable through said apertures at the other end.

10. An orthodontic bone anchor according to claim 9 wherein said one end is welded to said cap.

11. An orthodontic bone anchor according to claim 9 wherein said spring clip is L-shaped.

12. An orthodontic bone anchor according to claim 1 wherein said cap is angular in shape, wherein attachment means is insertable into said cap, wherein apertures are formed in said cap and said attachment means, and wherein a spring clip is attached to said cap and insertable through said apertures.

13. An orthodontic bone anchor according to claim 1 wherein an aperture is formed in said cap, a spring clip is attached to the emerging end of said bone anchor at one end and the other end being insertable into said aperture.

14. An orthodontic bone anchor comprising a bone plate, apertures formed in said bone plate for attachment to bone, a supragingival extension formed on one end of said bone plate, said extension angularly disposed with respect to said bone plate, a sliding cap enveloping said extension, the end of said extension remote from the junction between said extension and said bone plate extending beyond said sliding cap, an aperture formed in said end, and securing means disposed in said aperture.

15. An orthodontic bone anchor according to claim 14 wherein an elongated attachment is secured to said sliding cap and wherein the ends of said elongated attachment are disposed 90 degrees to the portion of said elongated attachment secured to said sliding cap.

16. An orthodontic bone anchor according to claim 15 wherein indentations are formed in said attachment.

* * * * *